(12) United States Patent
Carredano (10) Patent No.: US 11,670,402 B2
(45) Date of Patent: Jun. 6, 2023

(54) METHOD FOR PREDICTING THE CONDUCTIVITY OF A LIQUID MIXTURE

(71) Applicant: GE Healthcare Bio-Sciences AB, Uppsala (SE)

(72) Inventor: Enrique Carredano, Uppsala (SE)

(73) Assignee: CYTIVA SWEDEN AB, Uppsala (SE)

( * ) Notice: Subject to any disclaimer, the term of this patent is extended or adjusted under 35 U.S.C. 154(b) by 607 days.

(21) Appl. No.: 16/130,092

(22) Filed: Sep. 13, 2018

(65) Prior Publication Data

US 2019/0042704 A1    Feb. 7, 2019

Related U.S. Application Data

(62) Division of application No. 13/994,916, filed as application No. PCT/SE2011/051513 on Dec. 15, 2011, now abandoned.

(30) Foreign Application Priority Data

Dec. 17, 2010    (SE) .................................... 1051344-8

(51) Int. Cl.
*G16C 20/30*    (2019.01)
*G16C 99/00*    (2019.01)
(Continued)

(52) U.S. Cl.
CPC ............. *G16C 20/30* (2019.02); *B01D 15/12* (2013.01); *G01N 27/06* (2013.01);
(Continued)

(58) Field of Classification Search
CPC .... G06F 19/70; G01N 27/06; G01N 27/4166; G01N 30/34; B01D 15/12
See application file for complete search history.

(56) References Cited

U.S. PATENT DOCUMENTS

| 6,221,250 B1 | 4/2001 | Stafstrom |
| 8,271,139 B2 | 9/2012 | Bellafiore et al. |
| 2013/0270492 A1 | 10/2013 | Carredano |

FOREIGN PATENT DOCUMENTS

| CN | 101587150 A | 11/2009 |
| CN | 101726518 A | 6/2010 |

(Continued)

OTHER PUBLICATIONS

International Preliminary Report on Patentability received for PCT Patent Application No. PCT/SE2011/051513, dated Jun. 18, 2013, 9 pages.

(Continued)

*Primary Examiner* — Andrew J. Oyer
(74) *Attorney, Agent, or Firm* — Eversheds Sutherland (US) LLP (57) ABSTRACT

In a method of preparing a liquid solution by mixing ingredients according to a predetermined recipe, wherein at least one pair of species of the liquid solution is derived from a weak electrolyte and corresponds to an acid-base pair, the conductivity of the liquid solution is predicted by:

(i) for each pair of species derived from a weak electrolyte, solving a respective equilibrium equation to calculate the actual molar concentration of each such species at equilibrium in the liquid solution, (ii) calculating for each ionic species of said plurality of species the molar conductivity by the formula:

$$\Lambda = \Lambda_0 - K \times \mathrm{Sqrt}(c)$$

wherein $\Lambda$ is the molar conductivity, $\Lambda_0$ is the molar conductivity at infinite dilution, c is the concentration, and K is the Kohlrausch coefficient, and wherein K and $\Lambda_0$ are predetermined values for K and $\Lambda_0$ for each ionic species, (Continued)

(iii) calculating the conductivity $\kappa$ for each ionic species by the formula:

$$\kappa = c \times \Lambda$$

and (iv) adding up the conductivities determined in step (iii) for the different ionic species to obtain a predicted conductivity of the liquid solution. A computer program product comprises instructions for causing a computer to perform the method steps.

15 Claims, 1 Drawing Sheet

(51) Int. Cl.
  *G01N 27/06* (2006.01)
  *B01D 15/12* (2006.01)
  *G01N 27/416* (2006.01)
  *G01N 30/34* (2006.01)

(52) U.S. Cl.
  CPC ......... *G01N 27/4166* (2013.01); *G16C 99/00* (2019.02); *G01N 30/34* (2013.01)

(56) References Cited

FOREIGN PATENT DOCUMENTS

| EP | 2651547 A1 | 10/2013 |
|---|---|---|
| SI | 200800118 A | 5/2008 |
| SI | 22818 A | 12/2009 |
| WO | 2009131524 A1 | 10/2009 |
| WO | 2011037530 A1 | 3/2011 |
| WO | 2012/082061 A1 | 6/2012 |

OTHER PUBLICATIONS

International Search Report and Written Opinion received for PCT Patent Application No. PCT/SE2011/051513, dated Mar. 22, 2012, 14 pages.
Office Action received for European Patent Application No. 11848855.0, dated May 23, 2016, 6 pages.
Atkins et al., "Atkins Physical Chemistry", Higher Education Press, May 31, 2006, pp. 242, 833 & 834.
Chinese Supplementary Search Report for Chinese Application No. 201180060706 filed Dec. 15, 2011, 2 pages.
Atkins, P. et al., Atkins' Physical Chemistry, Oxford University Press, 2002, 7th Ed., p. 834-835.
Hirokazu Okamoto et al., "Theory and Computer Programs for Calculating Solution pH, Buffer, Formula, and Buffer Capacity for Multiple Component System at a Given Ionic Strength and Temperature," Pharmaceutical Research, vol. 14, No. 3, pp. 299-302, 1997.
Chandra, A. et al., Journal American Chem. Soc., 1999, vol. 121, pp. 4082-4083.
Debye, P. et al., Phys. Z. 1924, vol. 25, p. 49.
Onsager, L., Phys. Z, 1926, vol. 27, pp. 388-392.
Onsager, L., Phys. Z, 1927, vol. 28, pp. 277-298.
Guggenheim, E. A. et al., 1934, J. Phys. Chem., vol. 33, p. 533.
Li, D. et al., Analytical Chemistry, 1999, 71(3), pp. 687-699.
Dongmei Li et al., "Prediction of Electrophoretic Mobilities. 3. Effect of Ionic Strength in Capillary Zone Electrophoresis," Department of Chemistry, Anal. Chem., 1999, pp. 687-699.
European Search Report in corresponding Appl. No. 11848855.0 dated Jul. 4, 2016.
Chinese Office Action for CN Application No. 201910026056.7 dated Apr. 6, 2021 (21 pages with English translation).
Barrow, "The Physical Chemistry of Electrolytic Solutions," Reinhold Publishing Corporation, 1950, Section 22.2 Equivalent Conductance, pp. 620-423.

METHOD FOR PREDICTING THE CONDUCTIVITY OF A LIQUID MIXTURE

FIELD OF THE INVENTION

The present invention relates to the preparation of liquid mixtures, and more particularly to the preparation of a liquid mixture, such as a buffer, wherein the conductivity of the liquid mixture is predicted.

BACKGROUND OF THE INVENTION

A buffer solution is typically an aqueous solution consisting of a mixture of a weak acid and its conjugate base, or a weak base and its conjugate acid, and has the property that the pH of the solution changes very little when a small amount of strong acid or base is added to it. Buffer solutions are therefore used as a means of keeping pH at a nearly constant value in a wide variety of chemical applications, including e.g. chromatography, filtration, etc. In general, a buffer solution may be made up of more than one weak acid and its conjugate base. For instance, a wider buffer region may be created by mixing two buffering agents with overlapping individual buffer regions.

A buffer solution having a desired pH, and optionally also ionic strength, may be prepared by calculating the necessary amounts of the ingredients of the buffer and mixing them. While it is often necessary to solve several different equations for calculating the pH of a relatively simple mixture of a weak acid (or base) and a strong base (or acid) depending on their relative concentrations, there is commercial software available for performing such calculations. For many applications, it would be desirable to also be able to predict the expected conductivity of the buffer to be prepared. However, due to the complex nature of buffers solutions, being combinations of strong electrolytes like salts and strong acids or bases that dissociate completely and weak electrolytes like buffer substances that ionize partially, this has so far generally not been possible.

Atkins, P., and de Paula, J., *Atkins' Physical Chemistry*, Oxford University Press, 2002, $7^{th}$ Ed., p. 834-835 discloses calculation of the molar conductivity for a weak acid at equilibrium for the ideal case when activity coefficients are ignored.

It is an object of the present invention to provide a method of preparing a liquid mixture which comprises predicting the conductivity of the prepared liquid mixture wherein the activities of the ions are taken into account.

SUMMARY OF THE INVENTION

The above-mentioned object as well as other objects and advantages are achieved by the method according to the present invention for preparing a liquid mixture, especially a buffer solution, having a predicted conductivity.

According to the present invention, the prediction of the conductivity comprises solving the exact concentrations of the different ions present in solution including the equilibrium concentration of each of the charged species of a weak electrolyte, determining the molar conductivity of each of the charged species, calculating the corresponding conductivities, and summing up all the individual conductivities to obtain the total conductivity of the liquid mixture.

According to a basic feature of the invention, calculating the molar conductivities of the subspecies of the weak electrolyte includes applying predetermined values for the Kohlrausch coefficient used when calculating the molar conductivities. Typically, the predetermined Kohlrausch coefficient values are obtained by fitting measured conductivities to the equations used for determining molar conductivities.

In one aspect, the present invention therefore provides a method of preparing a liquid solution by mixing ingredients according to a predetermined recipe, wherein the liquid solution comprises a plurality of species, at least one pair of species being derived from a weak electrolyte and corresponding to an acid-base pair, and wherein the conductivity of the liquid solution is predicted by:

(i) for each pair of species derived from a weak electrolyte, solving a respective equilibrium equation to calculate from said predetermined recipe the actual molar concentration of each such species, including all ionic species derived from the weak electrolyte, at equilibrium in the liquid solution, (ii) calculating for each ionic species of said plurality of species the molar conductivity by the formula:

$$\Lambda = \Lambda_0 - K \times \mathrm{Sqrt}(c)$$

wherein $\Lambda$ is the molar conductivity, $\Lambda_0$ is the molar conductivity at infinite dilution, c is the concentration of the ionic species, K is the Kohlrausch coefficient, and Sqrt is square root, and wherein K and $\Lambda_0$ are obtained from a data set comprising predetermined values for K and $\Lambda_0$ for each ionic species, (iii) calculating the conductivity K for each ionic species by the formula:

$$\kappa = c \times \Lambda$$

wherein c and $\Lambda$ are as defined above, and (iv) adding up the conductivities determined in step (iii) for the different ionic species to obtain a predicted conductivity of the liquid solution.

In a preferred embodiment, the data set comprises values for the Kohlrausch coefficient K obtained by measuring the conductivity of a solution containing the ionic species at a plurality of different concentrations of the ionic species and different pH values, and optionally different temperatures, and fitting the resulting data to the formula in step (ii) above to obtain K.

Values for $\Lambda_0$ in the data set may include previously known values, such as literature values, and/or values be obtained by the fitting.

The Kohlrausch coefficient is typically expressed as $K = A + B \times \Lambda_0$, wherein A and B are temperature-dependent constants and $\Lambda_0$ is as defined above. Rather than obtaining K directly in the above-mentioned fitting, values for A and B may be obtained in the fitting, and K is then calculated therefrom.

Alternatively, the Kohlrausch coefficient may be expressed as $K = A + B + w \times \Lambda_0$, wherein A and B are temperature-dependent constants, w is the Onsager factor, and $\Lambda_0$ is as defined above. Values for A, B and w may then be obtained in the fitting and K calculated therefrom.

The concentration of each ionic species is preferably calculated by an algorithm comprising the equation of Debye-Hückel, wherein the ionic strength of each species is used as a weighting parameter in the calculation of an average hydrated radius of the ionic species, as will be described in more detail below.

The above-described method may advantageously be used for controlling a buffer formulation system or an in-line dilution system. The method may also be used in screening experiments wherein conductivity is used as a design of experiment (DoE) parameter.

Other preferred embodiments are set forth in the dependent claims.

In another aspect, the present invention provides a computer program product comprising instructions for performing the steps of the method aspect above.

The conductivity prediction steps in the method of the invention may further be used in a "backwards" fashion to indirectly determine pH of a solution by measuring its conductivity.

In still another aspect, the present invention therefore provides a device for measuring pH, comprising a conductivity sensor and means for calculating pH from measured conductivity using the conductivity prediction steps of the method aspect above in a backwards calculation mode.

Yet another aspect of the invention provides a method for predicting conductivity of a liquid solution comprising steps (i) to (iv) of the method aspect above.

In the following, the invention will be described in more detail, by way of example only, reference being made to the accompanying drawing.

DETAILED DESCRIPTION OF THE INVENTION

Unless defined otherwise, all technical and scientific terms used herein have the same meaning as commonly understood by a person skilled in the art related to this invention. Also, the singular forms "a", "an", and "the" are meant to include plural reference unless it is stated otherwise.

In order to facilitate an understanding of the disclosed invention, a number of terms will be defined below.

Definition

Buffer

As used herein, a buffer solution is an aqueous solution typically consisting of a mixture of a weak acid and its conjugate base or a weak base and its conjugate acid. It has the property that the pH of the solution changes very little when a small amount of strong acid or base is added to it. Buffer solutions are used as a means of keeping pH at a nearly constant value in a wide variety of chemical applications Titrand and Titrant As used herein in the context of buffer systems, a titrand is the solution (or other substance) into which a titrant is added. The titrand may, for example, be a weak acid or base, and the titrant a strong base or acid, respectively.

Electrolyte

A "strong" electrolyte is a solute that completely, or almost completely, ionizes or dissociates in a solution. These ions are good conductors of electric current in the solution. Examples of strong electrolytes include, for instance, salts, such as sodium chloride; strong acids, such as hydrochloric acid, sulfuric acid, nitric acid; and strong bases, such as potassium hydroxide, sodium hydroxide, calcium hydroxide.

A weak electrolyte, on the other hand, dissociates into ions only to a small extent, typically much less than 10%, and the vast bulk of the weak electrolyte remains in its original unionized form in solution. In general, most organic acids and their salts, and the salts of organic bases, are weak electrolytes. Examples of weak electrolytes include, for example acetic acid and citric acid and salts thereof. The amount of weak electrolyte that dissociates depends on the number of counter-ions present in the solution.

Conductivity (Electrolytic)

The conductivity (or specific conductance) of an electrolyte solution is a measure of its ability to conduct electricity. The SI unit of conductivity is "siemens" per meter (S/m).

Ionic Strength

The ionic strength of a solution is a function of the concentration of all ions in the solution (half the sum of concentration multiplied by the square of ionic charge for all ions). The ionic strength is typically given in the unit $mol/dm^3$.

Description of the Method of the Invention

As mentioned above, the present invention relates to the prediction of the conductivity of a buffer solution prepared according to a desired recipe or formula.

To prepare a buffer having a desired pH, the added amounts of moles of titrand, titrant, and salt solution, when required, can be calculated. From these mole values, the volume needed from corresponding stock solutions can in turn be calculated. Typically, such calculations are performed by suitable computer software, which is commercially available. The use of such software permits the preparation of buffers up to concentrations of 1 M or higher, as will be described in more detail below.

However, to predict the expected conductivity of the buffer to be prepared is not trivial. While for simple electrolytes like NaCl theoretical accounts have been developed (see e.g. Chandra, A., Biswas, R., and Bagchi, B., *J. Am. Chem. Soc.* 1999, 121, 4082-4083), this is generally not applicable to buffers which typically are complex combinations of, on the one hand, strong electrolytes like strong acids or bases and salts which dissociate completely, and weak electrolytes like buffer substances (weak acids and bases) that ionize partially. As mentioned above in the background section, Atkins, P., and de Paula, J., 2002 describes calculation of molar conductivities for weak electrolytes for the ideal case where activity coefficients are ignored, which assumption leads in most cases to gross errors in the solution of the equilibrium equations. There are, however, currently no models addressing the general case of real solutions where the activity of the ions is taken into account and data to parametrise such models.

Before describing the present invention in more detail, the theory behind electrolytic conductivity will be briefly described.

From its definition, the molar conductivity is given by the equation $$\Lambda = \kappa/c \qquad (\text{Eq. 1})$$

where $\kappa$ is the measured conductivity, and $c$ is the electrolyte concentration.

For strong electrolytes, such as salts, strong acids and strong bases, the molar conductivity is only weakly dependent on concentration and, to a good approximation, fits to the Kohlrausch equation $$\Lambda = \Lambda_0 - K \times \text{Sqrt}(c) \qquad (\text{Eq. 2})$$

where $\Lambda_0$ is the molar conductivity at infinite dilution, or "limiting molar conductivity", and K is the "Kohlrausch coefficient", which depends on the nature of the specific salt in solution.

The constant K can be expressed as $A + B \times \Lambda_0$ (Debye, P., Hückel, H., *Phys. Z.* 1924, 25, 49) or $A + B \times w \times \Lambda_0$ (Onsager, L., *Phys. Z,* 1926, 27, 388-392, and 1927, 28, 277-298), where A and B are constants depending on the temperature (T), dielectric constant (ε) and charges of the ions (A also depends on the viscosity of the liquid), and w is a factor introduced by Onsager which contains the contribution from self-Brownian motion of the ion (Onsager, L., 1926, 1927 above).

According to Equation 2 above, the molar conductivity Λ decreases as a function of the square root of the concentration in a linear fashion. This is an approximation that is valid in the low concentration regime. As the concentration increases, the rate of decrease of the molar conductivity Λ decreases so that it levels off, as can for instance be seen in FIG. 1 of the above cited reference Chandra, A., 1999. Besides, this reference also presents a microscopic theory that accounts for the constants A and B by treating the solvent as a dielectric continuum and calculating the concentration dependent ion contribution to microscopic friction.

The limiting molar conductivity $\Lambda_0$ can be decomposed into contributions from the different ions (commonly known as law of independent migration of ions):

$$\Lambda_0 = \Sigma_i v_i \lambda_i \qquad (\text{Eq. 3})$$

where $\lambda_i$ is the molar ionic conductivities of ion i, and $v_i$ is the number of ions i in the formula unit of the electrolyte (e.g. 2 and 1 for $Na^+$ and $SO_4^{2-}$, respectively, in $Na_2SO_4$).

A table of limiting molar conductivity of a limited number of different ions in solution can, for instance, be found in Harrison, R. D., Revised Nuffield Advanced Science Book of data. Longman, Harlow, 1984.

According to the present invention there is now suggested a novel approach for predicting conductivity, which is based, on the one hand, on the assumption that even if the buffering substance itself is not a strong electrolyte, every and each one of its charged subspecies can be considered as one strong electrolyte at equilibrium, and, on the other hand, on using the equilibrium concentrations to calculate the molar conductivities of the weak electrolyte subspecies from the Kohlrausch equation above, wherein the Kohlrausch coefficient K has been determined beforehand, typically by fitting measured conductivity data at known pH values and concentrations thereto.

Using this approach, in brief, by first determining the exact concentrations of the different ions present in solution including the concentration of each of the charged species of the buffer substance, the conductivity can then be calculated with Equations (2) and (3) above once the constants K and $\Lambda_0$, or alternatively the constants A, B and $\Lambda_0$ (and optionally w), have been determined. This determination can be made experimentally by measuring the conductivities of a large number of samples of the buffer at different concentrations, temperatures, and pH values, and then fitting the obtained data to Equation (2).

With regard to the first step of determining the concentrations of the different ions present in solution, methods to do this are documented in the literature and well known to persons skilled in the art and will therefore be only briefly addressed below. Basically this includes solving the equilibrium equations for the buffering species.

Solving Equilibrium Equations

For a particular basic species (which may be a base B or a conjugate base $A^-$) in equilibrium with a corresponding acidic species (which may be a conjugate acid $BH^+$ or an acid HA, respectively) the following equation applies $$pH = pK_a + \log \{(\text{basic species})/(\text{acidic species})\} \qquad (\text{Eq. 4})$$

which is often referred to as the Henderson-Hasselbach equation. In this equation, the parentheses denote the activity of each species rather than the concentration, the reason being that the ions involved tend to become shielded from the environment. The activity of each ion is related to the corresponding concentration through the activity coefficient φ

$$(\text{species}) = \varphi[\text{species}] \qquad (\text{Eq. 5})$$

In the ideal state of infinite dilution, φ becomes 1 and the activity of every ion will be equal to the corresponding concentration. However, in practice, the ionic strength is different from zero and the activity coefficients of the different species will be less than 1.

Inserting Eq. 5 into Eq. 4 above gives the pH in terms of the concentrations instead of activities $$pH = pK_a' + \log \{(\text{basic species})/(\text{acidic species})\} \qquad (\text{Eq. 6})$$

where $$pK_a' = pK_a + \log \varphi_b - \log \varphi_a \qquad (\text{Eq. 7})$$

in which $\varphi_a$ and $\varphi_b$ are the activity coefficients for the acidic and basic species, respectively, and $pK_a'$ is an apparent $pK_a$ value which allows the use of the measurable concentrations of the different buffer species.

A model for these deviations is given in the so-called Debye-Hückel theory, known as $$\log \varphi = (AZ^2 I^{0.5})/(1 + 0.33 \times 10^8 a I^{0.5}) \qquad (\text{Eq. 8})$$

wherein A is a constant, or rather a temperature dependent parameter ~0.51. Using well known data, the value of A can accurately be calculated as $A = 0.4918 + 0.0007 \times T + 0.000004 \times T^2$, where T is the temperature in degrees Celsius, Z is the charge of the ion and the quantity a, the radii of the hydrated ions (in Å), is described as the "mean distance of approach of the ions, positive or negative" in the original paper of Debye and Hückel.

The value of $pK_a'$ can be calculated by inserting Eq. 8 into Eq. 7 giving $$pK_a' = pK_a + (AZ_a^2 I^{0.5})/(1 + 0.33 \times 10^8 a_a I^{0.5}) - (AZ_b^2 I^{0.5})/(1 + 0.33 \times 10^8 a_b I^{0.5}) \qquad (\text{Eq. 9})$$

where the subscripts <u>a</u> and <u>b</u> specify the parameters corresponding to the acid and the base respectively, $Z_a$=charge of acidic species, $Z_b$=charge of basic species, $a_a$=ion size parameter of the acidic species, and $a_b$=ion size parameter of the basic species.

As to the parameter a, Guggenheim E. A. & Schindler, T. D., (1934) *J. Phys. Chem.* 33. 533 suggests an approximation of the parameter a set to 3 Å for all buffer molecules, leading to the simplified formula $$pK_a' = pK_a + (AZ_a^2 I^{0.5})/(1 + I^{0.5}) - (AZ_b^2 I^{0.5})/(1 + I^{0.5}) \qquad (\text{Eq. 10})$$

Eq. 10 above is the formula for ionic strength correction usually found in the literature.

Using Eq. 7 (or 4) in combination with the equations for (i) the conservation of mass, (ii) the conservation of charge, and (iii) the water dissociation equilibrium, the concentrations of the acidic and basic species, respectively, of a monoprotic buffer at equilibrium may be calculated.

However, many buffers are polyprotic, i.e. their buffer molecules can accept and give away more than one proton corresponding to more than one $pK_a$ value. The number of species in such a buffer system is always one more than the number of $pK_a$ values. The calculation of the amount of moles in each of the protonation species is equivalent to solving the equilibrium equations of each of the species with the "neighbouring" species with one more and/or one less proton and with the concentration of hydrogen atoms (the pH).

Assume, for example, a tritropic buffer. Four protonation states or species will be defined (s1, s2, s3 and s4), and three $pK_a$ values. Three equations (corresponding to three $pK_a$ values) may then be derived directly from Eq. 6 above.

$$xx[i]=10^{(pH-pKa[i])} \quad \text{(Eq. 11)}$$

where each i corresponds to each $pK_a(i)$ value (i=1, 2, 3), and xx[i] are the ratios between the concentrations of the corresponding base and the corresponding acid i.e. $xx[1]=[s_2/s_1]$, $xx[2]=[s_3/s_2]$, $xx[3]=[s_4/s_3]$.

In addition to these three equations, an equation arises because of the conservation of mass $$[s_1]+[s_2]+[s_3]+[s_4]=\text{buffer concentration} \quad \text{(Eq. 12)}$$

and the conservation of charge $$[H^+]-[OH^-]+\Sigma\text{specific charge }(s_i)-\text{titrant\_charge*}[\text{titrant}]-\text{spec\_charge(start\_species)*[start\_species]}=0 \quad \text{(Eq. 13)}$$

By "start_species" is meant the species of the buffer substance before mixing, i.e. the protonation state of the buffer in the can or stock solution. This protonation state is determined by the amount of counter-ions per buffer molecule because the macroscopic object, can or stock solution, has to be electrically neutral. The minus sign in front of [$OH^-$] is due to the minus sign of the charge of the OH ions, whereas the minus sign in front of the two last terms is due to the charge of the counter-ions of the titrant and the start_species, respectively.

Finally, there is the water dissociation equilibrium $$[OH^-][H^+]=10^{14} \quad \text{(Eq. 14)}$$

Equations (11) to (14) above imply that there are six equations with six unknowns (the four $[s_i]$, $[OH^-]$ and $[H^+]$) for the case of three $pK_a$ values, and the equilibrium concentrations of the respective acidic and basic species may thus be calculated.

For a monoprotic buffer, for example, the calculations are simplified; $s_1$ corresponds to the acidic species, $s_2$ to the basic species and the concentrations of $s_3$ and $s_4$ are set to zero.

A more accurate determination of the ion size parameter a in the Debye-Hückel equation 8 above is described in WO 2009/131524 A1 (the disclosure of which is incorporated by reference herein), where a is determined as the weighted mean ion size of all species contributing to the ionic strength of the liquid mixture, using the ionic strength as weighting parameter. The ion size parameter a may then be calculated as $$a = \frac{\sum I_i a_i}{I} \quad \text{(Eq. 15)}$$

where $I_i$ is the ionic strength, $a_i$ is the ion size parameter of species i, and I is the total ionic strength defined by $$I=\tfrac{1}{2}\Sigma(C_i Z_i) \quad \text{(Eq. 16)}$$

where $C_i$ is the concentration and $Z_i$ is the charge of ion present in the solution (in units of electronic charge), which gives $$I_i = \tfrac{1}{2} Z_i^2 C_i \quad \text{(Eq. 17)}$$

The ion size parameter a may also be approximated as $$a=0.5*(\text{mass})^{1/3}+\text{shell} \quad \text{(Eq. 18).}$$

where "shell" is fixed at a specific value for a positively charged ionic species (typically in the range of 3.9-4.1), and at another fixed value for a negatively charged species (typically in the range of 0-0.1, or 0).

This permits the determination of the relative proportions of the constituents of buffers having salt concentrations up to or above 2 M or even 5 M.

In the above-mentioned WO 2009/131524 A1 there is also disclosed a computer program, or software, for calculating a recipe (i.e. amounts of titrand, titrant, water and salt) to achieve a solution of a given pH and ionic strength (or, alternatively, salt concentration instead of ionic strength). Specifically, a computer program "Buffalo Plus" is disclosed which is written in Visual C++ and can be run in Windows for accurate calculation of buffer pH at ionic strengths as high as 1 M for buffer systems including phosphate, citrate, acetate and Tris.

Such software may conveniently be used for calculating the equilibrium concentrations of acidic and basic species for the purposes of the present invention.

Predicting Conductivity

1. Determination of the Kohlrausch Coefficient K

For each pair of ionic species of a weak electrolyte to be present in a buffer of a desired composition, pH, and optionally ionic strength, the conductivity of a solution containing the weak electrolyte is measured at a plurality of different concentrations and different pH values, and optionally different temperatures. The resulting conductivities are then used together with equilibrium concentrations obtained by solving equilibrium equations as described above to find through a computational procedure of regression analysis type the values for K that give the best fit to a regression model provided by the above-mentioned equations (2) and (3), i.e.

$$\Lambda=\Lambda_0-K\times\text{Sqrt}(c) \quad \text{(Eq. 2)}$$

$$\Lambda_0=\Sigma_i v_i \quad \text{(Eq. 3)}$$

Values for limiting molar conductivities are available in the literature for a number of common ions, including those of weak electrolytes. In cases, however, where such $\lambda_o$ values are not known, they may be determined in the fitting to equations (2) and (3).

Preferably, measurements are made for a large number a different weak electrolyte ionic species at different concentrations and pH to produce a catalogue or database of values for the coefficient K, optionally together with $\Lambda_o/\Lambda_o$ values.

2. Calculation of Conductivities

Values for K and $\Lambda_0$ obtained as described above are used to calculate the molar conductivity of each ion (strong electrolyte ions as well as weak electrolyte ions) present in the desired buffer solution using equation (2) above. The corresponding conductivity of each ion is then determined from the previously mentioned equation (1), i.e.

$$\Lambda=\kappa/c \quad \text{(Eq. 1),}$$

Finally, the conductivities of all ions are added up to give the predicted conductivity of the desired buffer solution.

The method of the invention may be implemented by software run on an electrical data processing device, such as a computer. Such software may be provided to the computer on any suitable computer-readable medium, including a record medium, a read-only memory, or an electrical or optical signal which may be conveyed via electrical or optical cable or by radio or other means.

Predicting conductivities as described above may be used for several purposes. Exemplary applications include the use for controlling a buffer formulation system or an in-line dilution system, wherein a buffer solution of predetermined conductivity, pH (and potentially other parameters) is prepared by mixing relative component proportions of at least one each of:
- a buffer;
- an acid or a base;
- a solvent;
- and optionally
- a salt, and wherein the relative component proportions are determined using predicted conductivity according to the present method and using predicted pH and Ionic strength in accordance with the method disclosed in WO 2009/131524. According to one embodiment the relative component proportions are determined using an iterative procedure wherein the conductivity and other control parameters are used to iteratively determine relative component proportions.

Such prediction of conductivities may also be used in screening experiments wherein conductivity is used as a design of experiment (DoE) parameter. Still another application is for determining the exact concentration of a stock solution of a weak electrolyte. Yet another application is for indirect measurement of pH by measuring conductivity and calculating pH therefrom.

The invention will now be described in more detail, by way of example only, by the following non-limiting Example.

Example

In this example, conductivities for a plurality of compositions of a formate buffer (formic acid—Na-formate) of different pH were predicted and compared with the measured conductivities.

Buffer solutions of different pH and salt concentration according to recipes calculated by using "Buffalo Plus" software (GE Healthcare) were prepared by weighing the respective amounts of the components and mixing in a TECAN robot according to Table 1 below. pH and conductivities were measured. Conductivities were measured using a WTWLF 340 conductivity meter, and the results are presented in Table 1. The temperature was 22° C.

TABLE 1

| pH | HCOOH (mole) | Na⁺HCOO⁻ (mole) | NaCl-conc. mole/dm³ | Buffer-conc. mole/dm³ | Measured conductivity mS/cm |
|---|---|---|---|---|---|
| 3.1 | 0.040791 | 0.009225 | 0 | 0.050016 | 1.32 |
| 3.97 | 0.0165223 | 0.0328 | 0 | 0.049322 | 3.17 |
| 2.995 | 0.20755 | 0.044107 | 0 | 0.251657 | 4.7 |
| 4.04 | 0.0651762 | 0.186358 | 0 | 0.251534 | 15.38 |
| 2.985 | 0.410651 | 0.093503 | 0 | 0.504154 | 9.1 |
| 4.06 | 0.115571 | 0.389142 | 0 | 0.504713 | 29.2 |
| 2.99 | 0.605233 | 0.148559 | 0 | 0.753792 | 13.62 |
| 4.095 | 0.15289 | 0.60327 | 0 | 0.75616 | 42.3 |
| 3.005 | 0.0410208 | 0.009768 | 0.251337 | 0.050789 | 27.3 |
| 3.9 | 0.0163126 | 0.034522 | 0.251337 | 0.050835 | 28.9 |
| 2.975 | 0.0406123 | 0.009823 | 0.502674 | 0.050435 | 51.1 |
| 3.885 | 0.015963 | 0.035611 | 0.503535 | 0.051574 | 52.5 |
| 3.035 | 0.0395468 | 0.012015 | 0.754871 | 0.051561 | 72.4 |
| 3.93 | 0.0140662 | 0.036802 | 0.754011 | 0.050868 | 73.8 |
| 3.005 | 0.200951 | 0.054151 | 0.250476 | 0.255102 | 30.4 |
| 4.04 | 0.0602869 | 0.192086 | 0.251337 | 0.252373 | 39.2 |
| 2.985 | 0.196017 | 0.054781 | 0.503535 | 0.250797 | 53.5 |
| 3.99 | 0.0628657 | 0.189574 | 0.502674 | 0.25244 | 61.3 |
| 2.995 | 0.193722 | 0.058587 | 0.754011 | 0.25231 | 74.3 |
| 4.035 | 0.0556598 | 0.194628 | 0.754011 | 0.250287 | 80.2 |

Using the Buffalo software, $pK_a'$ values and the equilibrium concentrations of HCOOH and Na⁺COO⁻, were then calculated, as well as the concentrations of Na⁺, H⁺, OH⁻ and Cl⁻, and the results are given in Table 2 below.

TABLE 2

| $pK_a'$ | HCOOH (mole/dm³) | COO⁻ (mole) | Na⁺ (mole/dm³) | H⁺ (mole/dm³) | OH⁻ (mole/dm³) | Cl⁻ (mole/dm³) |
|---|---|---|---|---|---|---|
| 3.7012 | 0.0399966 | 0.010019 | 0.00739624 | 0.000794328 | 1.25893E−11 | 0 |
| 3.66796 | 0.0164151 | 0.0329068 | 0.03402269 | 0.000107152 | 0.000107152 | 0 |
| 3.65565 | 0.206539 | 0.0451185 | 0.04511705 | 0.001011579 | 9.88553E−12 | 0 |
| 3.58292 | 0.065085 | 0.186449 | 0.18268706 | 9.12011E−05 | 1.09648E−10 | 0 |
| 3.62177 | 0.409616 | 0.094538 | 0.09763033 | 0.001035142 | 9.66051E−12 | 0 |
| 3.53232 | 0.115484 | 0.389229 | 0.37794773 | 8.70964E−05 | 1.14815E−10 | 0 |
| 3.59631 | 0.60421 | 0.149582 | 0.15384174 | 0.001023293 | 9.77237E−12 | 0 |
| 3.49858 | 3.49858 | 0.60335 | 0.57912539 | 8.03526E−05 | 1.24451E−10 | 0 |
| 3.57575 | 0.0400323 | 0.0107562 | 0.26169173 | 0.000988553 | 1.01158E−11 | 0.251337 |
| 3.56948 | 0.0161867 | 0.0346478 | 0.28905781 | 0.000125893 | 7.94328E−11 | 0.251337 |
| 3.53546 | 0.039553 | 0.0108823 | 0.51376836 | 0.001059254 | 9.44061E−12 | 0.502674 |
| 3.53138 | 0.0158327 | 0.0357414 | 0.54199543 | 0.000130317 | 7.67361E−11 | 0.503535 |
| 3.51002 | 0.0386243 | 0.0129371 | 0.76818423 | 0.000922571 | 1.08393E−11 | 0.754871 |
| 3.50728 | 0.0139487 | 0.036919 | 0.79395068 | 0.00011749 | 8.51138E−11 | 0.754011 |
| 3.56449 | 0.199963 | 0.0551394 | 0.3066874 | 0.000988553 | 1.01158E−11 | 0.250476 |
| 3.53586 | 0.0601957 | 0.192177 | 0.4414203 | 9.12011E−05 | 1.09648E−10 | 0.251337 |
| 3.52824 | 0.194982 | 0.0558156 | 0.56418415 | 0.001035142 | 9.66051E−12 | 0.503535 |
| 3.50969 | 0.0627634 | 0.189676 | 0.69719504 | 0.000102329 | 9.77237E−11 | 0.502674 |
| 3.50467 | 0.192711 | 0.0595988 | 0.81835827 | 0.001011579 | 9.88553E−12 | 0.754011 |
| 3.49041 | 0.0555676 | 0.19472 | 0.95075092 | 9.22571E−05 | 1.08393E−10 | 0.754011 |

The total conductivity $C_{tot}$ of the buffer solution is obtained by adding up the conductivities of all ionic species according to the formula:

$$C_{tot}=C_{s1}+C_{s2}+C_{Na+}+C_{H+}+C_{OH-}+C_{Cl-}$$

where the subscripts s1 and s2 denote HCOOH and Na⁺COO⁻, respectively.

The conductivity values are in turn obtained through equations (1) to (3) above, i.e.

$$\Lambda = \kappa/c \quad (\text{Eq. 1})$$

$$\Lambda = \Lambda_0 - K \times \text{Sqrt}(c) \quad (\text{Eq. 2})$$

$$\Lambda_0 = \Sigma_i v_i \lambda_i \quad (\text{Eq. 3})$$

$\Lambda_0$-values (in mSm² mol⁻¹) for the respective species are obtained from Atkins' Physical Chemistry, 7$^{th}$ Ed. (supra) and listed in Table 3 below.

TABLE 3

| Species | $\Lambda_0$ (mSm²mol⁻¹) |
|---|---|
| HCOOH | 0 |
| HCOO⁻, | 5.46 |
| Na⁺ | 5.01 |
| H⁺ | 34.96 |
| OH⁻ | 19.91 |
| Cl⁻ | 7.635 |

Using Equations (1) to (3) with the concentration values in Table 2 and the $\Lambda_0$-values in Table 3, a "manual" fitting procedure was used to obtain the respective values for the Kohlrausch coefficient K in Equation (2) that gives the best fit with the measured conductivity values in Table 1. More specifically, the fit was done manually in MS Office Excel by changing the parameters one by one gradually until the best fit had been obtained for a straight line through the origin in a graph where measured conductivity is plotted against predicted conductivity.

The resulting K-values for HCOO⁻, Na⁺ and Cl⁻ are indicated in Table 4 below together with the $\Lambda_0$ values. The K-values for HCOOH, H⁺ and OH⁻ were assumed to be zero due to low concentration.

TABLE 4

|  | HCOOH | HCOO⁻ | Na⁺ | H⁺ | OH⁻ | Cl⁻ |
|---|---|---|---|---|---|---|
| $\Lambda_0$ | 0 | 5.46 | 5.01 | 34.96 | 19.91 | 7.365 |
| K | 0 | 0.91 | 3.6 | 0 | 0 | 0.2 |

Corresponding conductivity values for the different species concentrations of each species indicated in Table 2, and the predicted total conductivity of the buffer solution, together with the measured conductivity values from Table 1, are given in Table 5 below.

TABLE 5

| Conductivity (mS/cm) | | | | | | |
|---|---|---|---|---|---|---|
| $C_{HCOOH}$ | $C_{COO-}$ | $C_{Na+}$ | $C_{H+}$ | $C_{Cl-}$ | $C_{tot}$ predicted | $C_{tot}$ measured |
| 0 | 0.537911 | 0.347652 | 0.277697 | 0 | 1.163261 | 1.32 |
| 0 | 1.74239 | 1.478616 | 0.03746 | 0 | 3.258467 | 3.17 |
| 0 | 2.376259 | 1.915369 | 0.353648 | 0 | 4.645275 | 4.7 |
| 0 | 9.447491 | 6.3416 | 0.031884 | 0 | 15.82097 | 15.38 |
| 0 | 4.897259 | 3.793084 | 0.361886 | 0 | 9.052229 | 9.1 |
| 0 | 19.04212 | 10.57049 | 0.030449 | 0 | 29.64306 | 29.2 |
| 0 | 7.640723 | 5.535201 | 0.357743 | 0 | 13.53367 | 13.62 |
| 0 | 28.67814 | 13.1484 | 0.028091 | 0 | 41.85464 | 42.3 |
| 0 | 0.577137 | 8.291416 | 0.345598 | 18.93757177 | 28.15172 | 27.3 |
| 0 | 1.833081 | 8.887061 | 0.044012 | 18.93757177 | 29.70173 | 28.9 |
| 0 | 0.583843 | 12.48254 | 0.370315 | 37.66637313 | 51.10307 | 51.1 |
| 0 | 1.889991 | 12.78929 | 0.045559 | 37.73027836 | 52.45512 | 52.5 |
| 0 | 0.692975 | 14.24782 | 0.322531 | 56.32268699 | 71.58601 | 72.4 |
| 0 | 1.951224 | 14.30905 | 0.041074 | 56.25926694 | 72.56062 | 73.8 |
| 0 | 2.892787 | 9.250744 | 0.345598 | 18.87312826 | 31.36226 | 30.4 |
| 0 | 9.726221 | 11.55717 | 0.031884 | 18.93757177 | 40.25285 | 39.2 |
| 0 | 2.927534 | 13.00987 | 0.361886 | 37.73027836 | 54.02956 | 53.5 |
| 0 | 9.604583 | 13.97224 | 0.035774 | 37.66637313 | 61.27897 | 61.3 |
| 0 | 3.121692 | 14.34849 | 0.353648 | 56.25926694 | 74.0831 | 74.3 |
| 0 | 9.849801 | 14.25905 | 0.032253 | 56.25926694 | 80.40037 | 80.2 |

Figure 1:
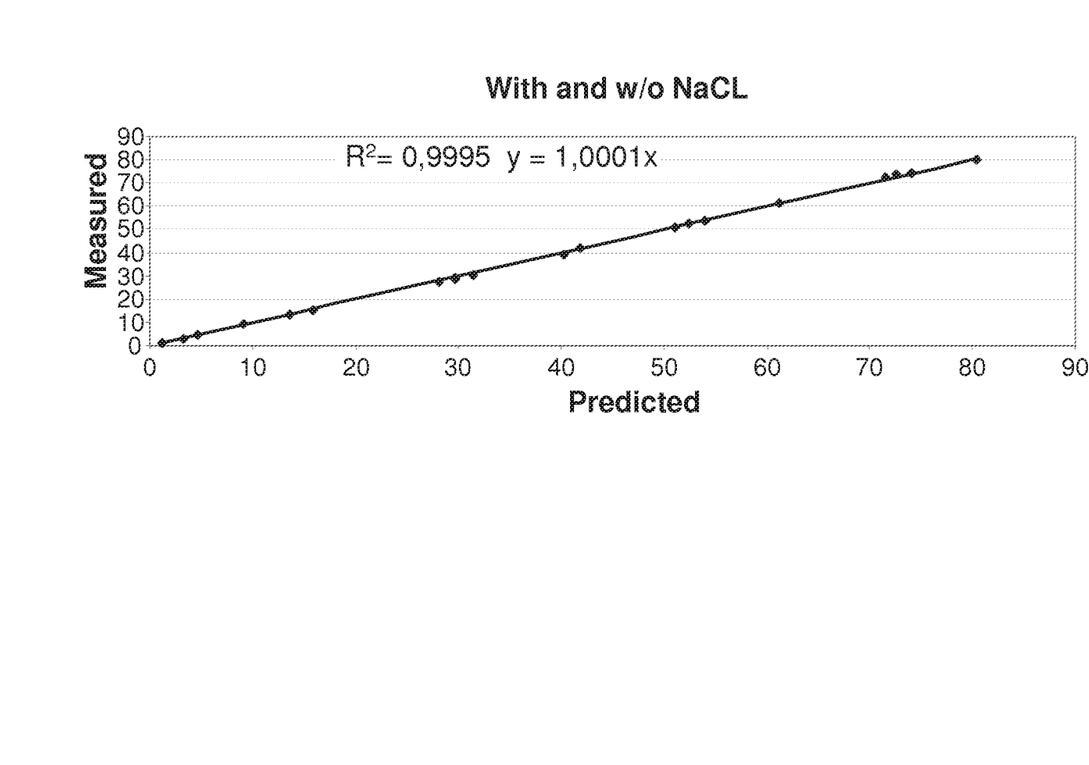
FIG. 1 is a graph showing measured conductivity versus predicted conductivity for a buffer solution.

The corresponding graph mentioned above where measured conductivity is plotted against predicted conductivity is shown in FIG. 1.

As apparent from Table 5 and FIG. 1, a good fit was obtained, which demonstrates that the procedure outlined above may be used for predicting the conductivity that will be obtained following a predetermined recipe for a buffer composition.

While the above described fitting procedure was done manually, it may conveniently be performed by an algorithm designed therefor. Based on the teaching above, the design of such a suitable algorithm may readily be made by a person skilled in the art.

The present invention is not limited to the above-described preferred embodiments. Various alternatives, modifications and equivalents may be used. Therefore, the above embodiments should not be taken as limiting the scope of the invention, which is defined by the appending claims.

What is claimed is:

1. A method implemented by a software run on a computer, for controlling a formulation system or an in-line dilution system of a liquid buffer solution, wherein the liquid buffer solution comprises a plurality of ionic species including at least one pair of weak electrolyte species (WES) that corresponds to an acid-base pair, the method comprising,
   (i) calculating the actual molar concentration of each WES (c') at equilibrium in the liquid buffer solution by solving Debye-Hückel equation where the ionic strength of each WES is used as a weighting parameter in the calculation of an average hydrated radius of the WES, (ii) determining Kohlrausch coefficient K of each WES by:
(1) making a series of standard liquid buffer solutions each comprising a plurality of ionic species, wherein the series of standard liquid buffer solutions have different concentrations and the plurality of the ionic species of the series of standard liquid buffer solutions are identical to the plurality of ionic species of the liquid buffer solution;
(2) measuring the conductivities of the series of standard liquid buffer solutions;
(3) calculating the actual molar concentration of each WES (c) at equilibrium in each of the standard liquid buffer solutions by solving Debye-Hückel equations where the ionic strength of each WES is used as a weighting parameter in the calculation of an average hydrated radius of the WES;
(4) treating each and every one of WES at equilibrium as one strong electrolyte and assuming the conductivity of each of the standard liquid buffer solution is the sum of conductivities of all ionic species in the standard solution;
(5) using equations (1) to (3) with the concentrations c obtained from (3) to calculate conductivities of the series of standard liquid buffer solutions; and
(6) fitting the calculated conductivities of the standard liquid solutions with respective conductivity of the standard liquid solutions measured in (2) to obtain Kohlrausch coefficient K of each WES, $$\Lambda = \kappa/c \qquad \text{(Eq. 1)}$$

$$\Lambda = \Lambda_0 - K \times \text{Sqrt}(c) \qquad \text{(Eq. 2)}$$

$$\Lambda_0 = \Sigma_i v_i \lambda_i \qquad \text{(Eq. 3)}$$

where $\Lambda$ is molar conductivity of each ionic species,
$\Lambda_0$ is predetermined molar conductivity at infinite dilution of each ionic species,
c is actual molar concentration of the ionic species,
K is Kohlrausch coefficient,
$\kappa$ is conductivity for each ionic species,
$v_i$ is the number of ionic species i in the formula unit of the electrolyte and
$\lambda_i$ is the molar ionic conductivities of the ionic species i, (iii) treating each and every one of WES at equilibrium as one strong electrolyte and calculating for each ionic species of said plurality of species the molar conductivity by the formula:

$$\Lambda = \Lambda_0 - K \times \text{Sqrt}(c')$$

(iv) calculating the conductivity $\kappa$ for each ionic species by the formula:

$$\kappa = c' \times \Lambda$$

wherein c' and $\Lambda$ are as defined above,
(v) adding up the conductivities determined in step (iv) for the different ionic species to obtain the predicted conductivity of the liquid buffer solution, and
(vi) controlling a buffer formulation system or an in-line dilution system by a software run on a computer, using the predicted conductivity to iteratively determine relative component proportions of the liquid buffer solution and mixing relative component proportions of at least one each of:

a buffer;
an acid or a base;
a solvent;
and a salt,
wherein one or more of the calculation steps are computer-implemented, the buffer is a formate buffer, and the fitting step (6) is done manually using a computer implemented spreadsheet.

2. The method of claim 1, wherein the Kohlrausch coefficient is expressed as $K = A + B \times \Lambda_0$, wherein A and B are temperature-dependent constants and $\Lambda_0$ is as previously defined, and wherein the predetermined values for K in the data set are calculated from values for A and B obtained by said fitting of step (ii).

3. The method of claim 1, wherein the Kohlrausch coefficient is expressed as $K = A + B + w \times \Lambda_0$, wherein A and B are temperature-dependent constants, w is the Onsager factor, and $\Lambda_0$ is as previously defined, and wherein the predetermined values for K in the data set are calculated from values for A, B and w obtained by said fitting of step (ii).

4. The method of claim 1, wherein the formate buffer solution further comprises sodium chloride.

5. A method implemented by a software run on a computer, for controlling a formulation system or an in-line dilution system of a liquid buffer solution, wherein the liquid buffer solution comprises a plurality of ionic species including at least one pair of weak electrolyte species (WES) that corresponds to an acid-base pair, the method comprising,
(i) calculating the actual molar concentration of each WES (c') at equilibrium in the liquid buffer solution by solving Debye-Hückel equation where the ionic strength of each WES is used as a weighting parameter in the calculation of an average hydrated radius of the WES,
(ii) determining Kohlrausch coefficient K of each WES by:
(1) making a series of standard liquid buffer solutions each comprising a plurality of ionic species, wherein the series of standard liquid buffer solutions have different concentrations and the plurality of the ionic species of the series of standard liquid buffer solutions are identical to the plurality of ionic species of the liquid buffer solution;
(2) measuring the conductivities of the series of standard liquid buffer solutions;
(3) calculating the actual molar concentration of each WES (c) at equilibrium in each of the standard liquid buffer solutions by solving Debye-Hückel equations where the ionic strength of each WES is used as a weighting parameter in the calculation of an average hydrated radius of the WES;
(4) treating each and every one of WES at equilibrium as one strong electrolyte and assuming the conductivity of each of the standard liquid buffer solution is the sum of conductivities of all ionic species in the standard solution;
(5) using equations (1) to (3) with the concentrations c obtained from (3) to calculate conductivities of the series of standard liquid buffer solutions; and
(6) fitting the calculated conductivities of the standard liquid solutions with respective conductivity of the standard liquid solutions measured in (2) to obtain Kohlrausch coefficient K of each WES, $$\Lambda = \kappa/c \qquad \text{(Eq. 1)}$$

$$\Lambda = \Lambda_0 - K \times \text{Sqrt}(c) \qquad \text{(Eq. 2)}$$

$$\Lambda_0 = \Sigma_i v_i \lambda_i \qquad \text{(Eq. 3)}$$

where $\Lambda$ is molar conductivity of each ionic species, $\Lambda_0$ is predetermined molar conductivity at infinite dilution of each ionic species, c is actual molar concentration of the ionic species,
K is Kohlrausch coefficient,
κ is conductivity for each ionic species,
$v_i$ is the number of ionic species i in the formula unit of the electrolyte and $\lambda_i$ is the molar ionic conductivities of the ionic species i, (iii) treating each and every one of WES at equilibrium as one strong electrolyte and calculating for each ionic species of said plurality of species the molar conductivity by the formula:

$$\Lambda = \Lambda_0 - K \times \mathrm{Sqrt}(c')$$

(iv) calculating the conductivity κ for each ionic species by the formula:

$$\kappa = c' \times \Lambda$$

wherein c' and Λ are as defined above, (v) adding up the conductivities determined in step (iv) for the different ionic species to obtain the predicted conductivity of the liquid buffer solution, and (vi) controlling a buffer formulation system or an in-line dilution system by a software run on a computer, using the predicted conductivity to iteratively determine relative component proportions of the liquid buffer solution and mixing relative component proportions of at least one each of:
a buffer;
an acid or a base;
a solvent;
and a salt, wherein one or more of the calculation steps are computer-implemented.

6. The method of claim 5, wherein the Kohlrausch coefficient is expressed as $K = A + B \times \Lambda_0$, wherein A and B are temperature-dependent constants and $\Lambda_0$ is as previously defined, and wherein the predetermined values for K in the data set are calculated from values for A and B obtained by said fitting of step (ii).

7. The method of claim 5, wherein the Kohlrausch coefficient is expressed as $K = A + B + w \times \Lambda_0$, wherein A and B are temperature-dependent constants, w is the Onsager factor, and $\Lambda_0$ is as previously defined, and wherein the predetermined values for K in the data set are calculated from values for A, B and w obtained by said fitting of step (ii).

8. The method of claim 5, wherein the buffer is a formate buffer.

9. The method of claim 5, wherein the fitting step (6) is done manually using a computer implemented spreadsheet.

10. The method of claim 5, wherein the buffer is a phosphate, citrate, acetate, or Tris buffer.

11. The method of claim 5, wherein the value of $\Lambda_0$ for each ionic species is obtained from published literature.

12. The method of claim 1, further comprising calculating and determining the pH of the liquid buffer solution from the predicted conductivity.

13. The method of claim 1, implemented by a software run on a computer, further comprising using the predicted conductivity, as a design of experiment (DoE) parameter, for determining the exact concentration of a stock solution of a weak electrolyte.

14. The method of claim 5, further comprising calculating and determining the pH of the liquid buffer solution from the predicted conductivity.

15. The method of claim 5, implemented by a software run on a computer, further comprising using the predicted conductivity, as a design of experiment (DoE) parameter, for determining the exact concentration of a stock solution of a weak electrolyte.

* * * * *